US008900623B2

(12) United States Patent
Lee

(10) Patent No.: US 8,900,623 B2
(45) Date of Patent: Dec. 2, 2014

(54) STICKY SOFT GEL FOR TREATING POULTRY

(75) Inventor: Eng-Hong Lee, Guelph (CA)

(73) Assignee: Vetech Laboratories Inc., Guelph (CA)

( * ) Notice: Subject to any disclaimer, the term of this patent is extended or adjusted under 35 U.S.C. 154(b) by 87 days.

(21) Appl. No.: 13/387,362

(22) PCT Filed: Jul. 27, 2010

(86) PCT No.: PCT/CA2010/001156
§ 371 (c)(1),
(2), (4) Date: Jan. 26, 2012

(87) PCT Pub. No.: WO2011/011873
PCT Pub. Date: Feb. 3, 2011

(65) Prior Publication Data
US 2012/0121644 A1 May 17, 2012

(30) Foreign Application Priority Data

Jul. 28, 2009 (CA) .................................... 2674143

(51) Int. Cl.
| | | |
|---|---|---|
| A61K 47/00 | (2006.01) | |
| A61K 9/14 | (2006.01) | |
| A61K 39/17 | (2006.01) | |
| A61K 39/215 | (2006.01) | |
| A61K 39/00 | (2006.01) | |
| A61K 39/155 | (2006.01) | |
| A61K 39/235 | (2006.01) | |
| A61K 39/112 | (2006.01) | |
| A61K 39/02 | (2006.01) | |
| A61K 39/002 | (2006.01) | |
| A61K 39/12 | (2006.01) | |
| A23K 1/16 | (2006.01) | |
| A23K 1/00 | (2006.01) | |
| A23K 1/18 | (2006.01) | |
| A23L 1/05 | (2006.01) | |
| A61K 9/00 | (2006.01) | |
| A61K 9/06 | (2006.01) | |
| A61K 9/70 | (2006.01) | |
| A61K 47/36 | (2006.01) | |

(52) U.S. Cl.
CPC .............. *A23K 1/1643* (2013.01); *A23K 1/002* (2013.01); *A23K 1/1826* (2013.01); *A23L 1/05* (2013.01); *A61K 9/0095* (2013.01); *A61K 9/06* (2013.01); *A61K 9/7015* (2013.01); *A61K 39/0275* (2013.01); *A61K 39/12* (2013.01); *A61K 39/17* (2013.01); *A61K 47/36* (2013.01); *C12N 2760/18134* (2013.01)

USPC ................... 424/439; 424/214.1; 424/221.1; 424/229.1; 424/211.1; 424/233.1; 424/258.1; 424/264.1; 424/265.1; 424/204.1; 424/484; 424/485; 424/488; 424/489; 424/500

(58) Field of Classification Search
CPC ... A23K 1/002; A23K 1/1643; A23K 1/1826; A23L 1/05; A61K 31/407; A61K 31/7016; A61K 33/30; A61K 35/48; A61K 35/50; A61K 35/51; A61K 39/0275; A61K 39/12; A61K 39/17; A61K 45/06; A61K 9/06; A61K 9/1617; A61K 9/1623; A61K 9/1694; A61K 9/19; A61K 9/7015; A61K 6/00; C12N 2760/18134; C12N 1/00
See application file for complete search history.

(56) References Cited

U.S. PATENT DOCUMENTS

| | | | |
|---|---|---|---|
| 2003/0157135 A1 * | 8/2003 | Tsuji et al. ................. | 424/278.1 |
| 2005/0095336 A1 | 5/2005 | Maletto | |
| 2009/0191307 A1 * | 7/2009 | Holzgraefe et al. ............. | 426/2 |

FOREIGN PATENT DOCUMENTS

| | | | |
|---|---|---|---|
| CA | 2222515 | | 12/1996 |
| CA | 2222515 | A1 * | 12/1996 |
| CA | 2530843 | | 1/2005 |
| CA | 2569684 | | 12/2005 |
| EP | 1911464 | | 4/2008 |
| JP | 2008099640 | | 5/2008 |
| KR | 20030093471 | | 12/2003 |
| KR | 100853301 | | 8/2008 |
| WO | WO2005/004989 | * | 1/2005 |
| WO | WO2005099617 | | 10/2005 |

OTHER PUBLICATIONS

Juul-Madsen et al., Poultry Science, 2006, 85:986-998.*
Bermudez, A.J. and B. Stewart-Brown, 2003. Disease prevention and diagnosis. In: Diseases of Poultry, 11th Edn., Iowa State Press, Ames, IA, pp. 30-36.

* cited by examiner

*Primary Examiner* — Nicole Kinsey White
(74) *Attorney, Agent, or Firm* — Wolf, Greenfield & Sacks, P.C.

(57) ABSTRACT

The present invention is directed to a composition, kit and method for delivering a soft flowable gel to a flock of poultry in barns, but can also be used in hatcheries or free range farms, for treating poultry with a therapeutic agent. The soft flowable gel comprises water, a gelling agent, a therapeutic agent and between about 0.05% and 0.15% xanthan gum.

16 Claims, No Drawings

STICKY SOFT GEL FOR TREATING POULTRY

CROSS REFERENCE TO RELATED APPLICATIONS

This application is a National Phase entry of International Patent Application Serial No. PCT/CA2010/001156 filed 27 Jul. 2010, and claims the benefit of priority of U.S. patent application Ser. No. 12/510,926 filed 28 Jul. 2009 and claims the benefit of priority of Canadian Patent Application No. 2,674,143 filed 28 Jul. 2009.

FIELD OF THE INVENTION

The present invention relates to a sticky soft gel for treating a flock of poultry, particularly poultry in a barn, and also poultry in a hatchery or free range farm. In particular, the present invention relates to a sticky soft gel for use in delivery of a therapeutic agent, particularly a viral, bacterial or protozoan vaccine to a flock of poultry in a barn.

BACKGROUND OF THE INVENTION

There are many circumstances where poultry must be treated such as by administration of therapeutic agents. There are many therapeutic agents which are used in the raising of poultry: vaccines, competitive exclusion products, vitamins, minerals, medicaments and many others. A number of such therapeutic agents must be protected from environmental effects while being delivered to the poultry.

In particular, poultry are required to be immunized against various diseases and the type of vaccine used for each disease dictates its method of administration. Vaccines may be administered in the hatchery by injection at the time of sorting of the hatchlings from the incubator into holding or transporting trays. Live vaccines may also be administered once the hatchlings are established in their brooding areas in the form of aqueous suspensions, either sprayed on feed or added to the drinking water.

Examples of live vaccines that are used to immunize poultry include viral vaccines such as Hemorrhagic Enteritis Virus (HE), Infectious Bursal Disease Virus (IBD) and Newcastle Disease Virus (ND). Such vaccines are, at present, comprised of an attenuated strain of the virus in a suitable carrier for administration. Other viral vaccines include Infectious Bronchitis, Infectious Laryngotracheitis, *Mycoplasma* sp., and Pneumoviruses. Live bacterial vaccines, such as *Salmonella* vaccine, and protozoan vaccines, such as coccidiosis vaccine, are also used to immunize poultry.

One method of administering vaccine in the hatchery is through the use of a spray cabinet, which is utilized to spray the hatchlings with a liquid form of the vaccine. A flat or tray of hatchlings usually containing about 100 birds is placed in the spray cabinet and a predetermined dose of liquid vaccine is sprayed directly on the birds. It is expected that as the birds preen they will ingest the vaccine from their feathers. This method suffers some drawbacks in that uniform exposure of all of the hatchlings may not be easily achieved. In addition, as the birds are being sprayed with a water-suspended vaccine, there is a risk that some hatchlings may be chilled more than others leading to the staggering of vaccine uptake or loss of uniform exposure. Moreover, chilled hatchlings increase early mortality.

In my previous patent application WO 05099617 published Oct. 27, 2005 I described a soft gel delivery system for treating poultry hatchlings in a hatchling tray, in particular, an apparatus for immunizing poultry hatchlings against coccidiosis utilizing a soft gel vaccine. While the apparatus was useful in the hatchery, once the poultry are established in the barn, such apparatus is not easily used as a delivery system. Furthermore, if a soft gel used to treat poultry in a barn is not sufficiently sticky, the gel beadlets can more easily roll off the feathers of the birds onto the floor, thereby reducing the availability of the beadlets for the birds' consumption.

One common method of immunization in the barn involves the use of on-feed spray administration while the birds are feeding. A vaccine using water as a carrier is sprayed onto the feed to be provided to the poultry. The use of on-feed spray administration requires large doses of vaccine to overcome waste. Uniform exposure of the flocks to the vaccine cannot always be achieved. Although coccidia, for example, can be sprayed on feed, viral and bacterial vaccines that are highly attenuated are not hardy enough to withstand the dry surfaces of feed.

Vaccine may also be administered through the use of drinking water systems or through water proportioning systems including automatic fountains and automatic water medicator or proportioners. However, given the susceptibility of viral vaccines to chlorine and other disinfectants commonly used in poultry barns, the water lines have to be cleaned or flushed before administration of the vaccine. Additionally, administration of the vaccine through the water lines requires that after administration, the water lines must remain chlorine free sometimes for up to 24 hours to allow the safe consumption of the rest of the vaccine.

Thus, there remains a need for a simplified means for administration of therapeutic agents in soft gel form to poultry beyond the hatchling stage, where the administration of such therapeutic agent must wait until the negating effect of the maternally derived antibodies (MDA) have waned or disappeared.

SUMMARY OF THE INVENTION

The present invention is directed to a composition and method for delivering a soft flowable gel to poultry in barns for treating the poultry with a therapeutic agent. Various embodiments of the present invention may also be used on free range farms or in a hatchery.

One aspect of the invention relates to a soft flowable gel composition comprising between about 0.5% and 2.5% w/v of one or more gelling agents, (gelling agents such as in the 60/40 gel diluent of Vetech Laboratories Inc. or the Water diluent of Vetech Laboratories Inc.) and more particularly about 0.5% and 1.5% w/v of one or more gelling agents and sufficient numbers of an live immunogenic organism to provide for protection of the poultry from infection by the wild type organism in a volume of the gel composition normally consumed by poultry in a predetermined time. Another aspect of the present invention relates to a dry powder mixture for suspension in water to form a sticky soft flowable gel for treating a flock of poultry, the dry powder mixture comprising: a) a sticky gum selected from the group consisting of xanthan gum, guar gum, gum arabic and locust bean gum. Another aspect of the present invention relates to a dry powder mixture for suspension in water to form a sticky soft flowable gel for treating a flock of poultry, the sticky soft flowable gel having a therapeutic agent dissolved or suspended therein, the dry powder mixture comprising: a) a sticky gum selected from the group consisting of xanthan gum, guar gum, gum arabic and locust bean gum. Yet another aspect of the present invention relates to a dry powder mixture wherein a) the sticky gum is xanthan gum provided in an amount to constitute about 0.05-0.15% w/v of the soft flowable gel. Another aspect of the present invention relates to a dry powder mixture wherein a) the sticky gum is xanthan gum provided in an amount to constitute about 0.05-0.15% w/v of the soft flowable gel, and further comprises carrageenan and/or maltodextrin. Yet another aspect of the present invention relates to a dry powder mixture comprising a) a sticky gum which is xanthan gum provided in an amount to constitute about 0.05-0.15% w/v of the soft flowable gel, and carrageenan and maltodextrin, wherein the carrageenan and the maltodextrin in combination are provided in an amount to constitute about 0.5-2.5% w/v of the sticky soft flowable gel. In another aspect, the present invention relates to a dry powder mixture comprising a) a sticky gum which is xanthan gum provided in an amount to constitute about 0.05-0.15% w/v of the soft flowable gel, and carrageenan and maltodextrin wherein one of the carrageenan and the maltodextrin is provided in an amount to constitute about 1.5-1.75% w/v of the sticky soft flowable gel, and the other of the carrageenan and the maltodextrin is provided in an amount to constitute about 0.5-0.75% w/v of the sticky soft flowable gel. In another aspect, the present invention relates to a dry powder mixture as described herein further comprising carboxymethyl cellulose in an amount to constitute about 0.05-0.125% w/v of the sticky soft flowable gel. Another aspect of the present invention relates to kits and sticky soft flowable gels made from the dry powder mixtures described herein, wherein the soft flowable gels are reconstituted from the dry powder mixtures.

Another aspect of the present invention relates to a sticky soft flowable gel composition for treating a flock of poultry comprising: a) xanthan gum in an amount of about 0.05% to 0.15% w/v, b) carrageenan, c) water, and d) a therapeutic agent. Another aspect of the present invention relates to a sticky soft flowable gel composition or a kit for making a sticky soft flowable gel having a therapeutic agent which is a therapeutically effective amount of at least one therapeutic agent selected from the group consisting of a) a live organism selected from the group consisting of Hemorrhagic Enteritis Virus (HE), Infectious Bursal Disease Virus (IBD), Newcastle Disease Virus (ND), *Salmonella*, Infectious Bronchitis, Infectious Laryngotracheitis, *Mycoplasma* sp., a Pneumovirus, Coccidiosis, and a competitive exclusion product, such as probiotics, *lactobacillus* or *bacillus* species, b) vitamins, c) minerals, and d) electrolytes. Another aspect of the present invention relates to a kit for treating a flock of poultry comprising a dry powder mixture in a first container, wherein the dry powder mixture is for suspension in water to form a sticky soft flowable gel, and a therapeutic agent in the first container or in a second container, wherein the therapeutic agent is for dissolution or suspension in the sticky soft flowable gel, the dry powder mixture comprising: a) a sticky gum selected from the group consisting of xanthan gum, guar gum, gum arabic and locust bean gum. Another aspect of the present invention relates to a kit for treating a flock of poultry, the kit comprising a dry powder mixture in a first container, wherein the dry powder mixture is for suspension in water to form a sticky soft flowable gel, the sticky soft flowable gel having a therapeutic agent dissolved or suspended therein, the dry powder mixture comprising: a) a sticky gum selected from the group consisting of xanthan gum, guar gum, gum arabic and locust bean gum. In another aspect, the present invention relates to kits as described herein comprising xanthan gum provided in an amount to constitute about 0.05-0.15% w/v of the soft flowable gel. In another aspect, the present invention relates to a method of treating a flock of poultry with a sticky soft flowable gel, the sticky soft flowable gel having a therapeutic agent dissolved or suspended therein, the method comprises providing the sticky soft flowable gel comprising about 0.05% to 0.15% w/v xanthan gum, carrageenan and maltodextrin, wherein the carrageenan and maltodextrin in combination are provided in an amount to constitute about 0.5-2.5% w/v of the sticky soft flowable gel, wherein the sticky soft flowable gel is capable of being dispensed through a manifold nozzle arrangement; providing a beadlet dispensing apparatus; the apparatus being capable of delivering a predetermined volume of the sticky soft flowable gel from a reservoir through the manifold nozzle arrangement, dispensing the predetermined volume of the sticky soft flowable gel as small beadlets onto the poultry and allowing the poultry to consume the beadlets.

In another aspect of the invention the soft flowable gel composition comprises a combination of a carrageenan and a xanthan gum gelling agent.

In yet another aspect of the invention, the composition is reconstituted from a dry powder mixture containing about 20-30% w/w maltodextrin, 60-70% carrageenan (kappa carrageenan), 2-6% xanthan gum and 2-5% carboxymethyl cellulose. In yet another aspect of the invention, the composition is a water diluent reconstituted from a dry powder mixture containing about 20-30% w/w carrageenan (lambda carrageenan), 60-70% maltodextrin, 2-6% xanthan gum and 2-5% carboxymethyl cellulose.

In yet another aspect of the invention the composition is reconstituted from a dry powder mixture containing about 25% maltodextrin, 67% carrageenan, 4% xanthan gum and 4% carboxymethyl cellulose.

In yet another aspect of the invention there is provided a kit for immunizing poultry in a barn, the kit comprising a mixture of one or more gelling agents provided as a dry powder in a first vial and a composition of a sufficient number of live immunogenic organisms to immunize the poultry and a pharmaceutically acceptable excipient in a second vial.

In a further aspect of the invention, the kit also includes instructions to reconstitute the gelling agents and live immunogenic organisms, mix the reconstituted agents and organisms and administer them to poultry in a barn.

In yet another aspect of the invention, the one or more gelling agents together with xanthan gum are provided as a dry powder mixture containing about 20-30% maltodextrin, 60-70% carrageenan (mainly kappa carrageenan), 2-5% carboxymethyl cellulose and 2-6% xanthan gum (this mixture was made by using 60/40 gel diluent of Vetech Laboratories Inc., to which the xanthan gum was added).

In yet another aspect of the invention the one or more gelling agents together with xanthan gum are provided as a dry powder mixture containing about 25% maltodextrin, 67% carrageenan, 4% xanthan gum and 4% carboxymethyl cellulose (60/40 diluent of Vetech Laboratories Inc., to which xanthan gum was added). In yet another aspect of the invention the one or more gelling agents together with xanthan gum are provided as a dry powder mixture containing about 25% carrageenan, 67% maltodextrin, 4% xanthan gum and 4% carboxymethyl cellulose (Water diluent of Vetech Laboratories Inc., to which xanthan gum was added).

In another aspect, the present invention is directed to a method of treating poultry with a viral vaccine. The method comprises providing the viral vaccine in a soft gel suspended in water and capable of being dispensed through a nozzle arrangement; providing a spray dispensing apparatus; the apparatus being capable of delivering a predetermined volume of the gel from a reservoir through the manifold nozzle arrangement, dispensing the predetermined volume of the soft gel as small beadlets onto the poultry and allowing the poultry to consume the beadlets.

DETAILED DESCRIPTION OF THE PREFERRED EMBODIMENTS

The present invention is directed to a sticky soft flowable gel, and dry powder mixtures and kits for making the soft flowable gel, for delivery to poultry in barns for treating the poultry. Various embodiments of the present invention may also be used on free range farms or in a hatchery. In a preferred embodiment, the soft gel contains a uniform suspension of a therapeutic agent and in a particularly preferred embodiment, the therapeutic agent is a viral vaccine and the delivery system delivers the vaccine in beadlets of the soft gel to the poultry for the purpose of immunizing the poultry in the barn. The soft flowable gel is capable of being pumped and delivered directly to the poultry. The soft flowable gel is dispensed as a plurality of small beadlets which contain the therapeutic agent and which are easily capable of being ingested by the poultry. The gel beadlets retain their moisture content to maintain the viability and/or efficacy of the therapeutic agent contained in the soft gel during the dispensing and consumption of the soft gel. The beadlets help to prevent the moisture from escaping and minimize the potential wetting of the birds.

The soft flowable gel utilizes a suitable gelling agent that can form the soft gel at relatively low concentrations to allow the soft gel to contain mostly water. Preferably at least 90% by weight of the gel is water, more preferably at least 95% by weight and most preferably about 97%-98% by weight. The suitable gelling agent is preferably a polysaccharide gelling agent which gels rapidly to maintain the therapeutic agent in a relatively uniform dispersion throughout the soft flowable gel. More preferably the gelling agent is a carrageenan or alginate gelling agent. Most preferably, the gelling agent is a kappa or lambda carrageenan gelling agent.

The soft flowable gel provides for an easy to handle method of treating poultry and is, therefore, suitable for general workers without any special expertise required. The soft flowable gel is produced utilizing an edible gelling polysaccharide gel, preferably an alginate or carrageenan gel, more preferably a lambda or kappa carrageenan gel and most preferably a water soluble lambda-type carrageenan extracted from the red algae *Eucheuma cottonii*.

The soft flowable gel is prepared by dissolving the gel powder in water at a suitable temperature to effect dissolution of the polysaccharide powder. The powder is added to the water at a concentration such that, when mixed with any therapeutic agent and allowed to gel, a soft flowable gel results. Typically, for gels containing therapeutic agents, the dissolved gel powder and therapeutic agent are mixed at a ratio of gel powder to therapeutic agent sufficient to produce the soft flowable gel having the therapeutic agent uniformly suspended therein. For highly soluble agents administered at low doses the ratio may be as high as 1,000:1 (V/V) of dissolved gel powder to therapeutic agent. For large particulate therapeutic agents, such as organisms used for immunization or competitive exclusion products, the ratios will generally be in the range of dissolved gel powder to the therapeutic agent of about 1:1 (V/V) to about 20:1 (V/V). Suitable such soft flowable gels have been found to have a final concentration of the edible polysaccharide in the gel form of between about 0.5 and 2.5 percent, preferably between about 0.5 and 1.5 percent, preferably between about 0.6 and 1.5 percent, more preferably between about 0.6 and 1 percent, even more preferably between about 0.8 and 1.0 percent and most preferably about 1.0 percent. Thus preferably, where the ratio of dissolved gel powder to therapeutic agent is about 100:1 (V/V), a dissolved polysaccharide gel solution of about 0.6 and 1.5 percent, preferably between about 0.6 and 1 percent, more preferably between about 0.8 and 1.0 percent and most preferably about 1.0 percent, is mixed with a suspension of therapeutic agent and the mixture is allowed to gel.

The soft flowable gel when used as a vaccine has sufficient levels of the immunizing organisms to provide immunization to the flock. It has been found that for the method of the present invention about 15 to 50 ml of gel for every 100 hatchlings is used, for chicken hatchlings, preferably about 20 to 30 ml, more preferably about 20 to 25 ml, most preferably about 25 ml of the gel while for turkey hatchlings, preferably about 20 to 40 ml, more preferably 25 to 35 ml, most preferably 35 ml. In a barn, the birds are larger and it has been found that for the method of the present invention about 25 ml to 50 ml of gel for chicks, and 50 ml to 100 ml of gel for turkey poults, for every 100 birds is needed. The concentration of the immunizing organisms in the gel should be such as to provide sufficient organisms in this typical volume to immunize the poultry. It has been found that for most viral vaccines between about 0.1 and 100 $EID_{50}$ per bird provides adequate protection and so it is preferred if the soft gel has between about 1 and 200 $EID_{50}$ per ml of gel, to provide for proper immunization of the flock. Preferably, the soft gel vaccine contains between about 5 and 100 $EID_{50}$ per ml of gel, most preferably about 50 $EID_{50}$ per ml of gel. For a soft gel prepared by mixing the dissolved polysaccharide powder with the viral suspension in a ratio of about 100:1 (V/V), 100 volumes of a 0.6 to 1.5 percent polysaccharide gel solution is mixed with one volume of viral suspension containing between about 10 and 10,000 $EID_{50}$ per ml, more preferably 100 volumes of a 0.6 to 1.5 percent polysaccharide solution with one volume of viral suspension containing between about 500 and 10,000 $EID_{50}$ per ml, most preferably 100 volumes of a 1.0 percent solution of polysaccharide solution is mixed with one volume of viral suspension containing about 5,000 $EID_{50}$ per ml. All of the above percentages are by weight.

The use of the edible polysaccharide gels results in a gel which gels rapidly, generally at the completion of mixing, in about 5 minutes or less. This maintains any therapeutic agents such as vaccine organisms in uniform suspension and allows for more uniform exposure of the poultry to the therapeutic agents. Unlike suspension in water, the therapeutic agents in the soft gel, after preparation with a mixer can remain suspended without further agitation for up to 24 hours.

This rapid uptake of the therapeutic agents in 5 minutes or less allows the barn administration to be accomplished in as short as a couple of hours: one hour of water starvation each before and after the administration of the therapeutic agents instead of the 24 hours or more sometimes required by the prior art method of water administration.

The low content of the edible gum in the soft gel means that preferably 95% by weight or more of the gel is water which, when used with or without therapeutic agents, can aid in the hydration of the bird. The soft gel has other advantages over liquid suspensions in that the gel will not wet the bird as much and therefore will not affect the health of the birds, particularly in winter when, if the bird becomes wet through exposure to aqueous solution, the exposure may cause death of the bird.

The therapeutic agent utilized with the soft flowable gel of the present invention may also include one or more of vitamins, minerals, competitive exclusion products, etc. The soft flowable gel of the present invention is particularly useful for administration of live organisms, such that are used in competition exclusion products or vaccines. Competitive exclusion products are probiotics, for example, such as *Lactobacillus acidophilus*, which are utilized to populate the gut of the poultry and help minimize the potential infection of the poultry with pathogenic organisms, such as *Salmonella*, Clostridia, etc. One example of such a competitive exclusion product is sold by Orion Corp., Finland under the trade name Broilact.

The soft flowable gel of the present invention is preferably utilized for administration of live vaccines, particularly live viral and bacterial vaccines. In one aspect the soft flowable gel is utilized for the administration of live bacterial vaccines such as *Salmonella*. In a preferred embodiment, the soft flowable gel is most preferably utilized for administration of live viral vaccines to poultry. Such vaccines may include live Infectious Bursal disease, Newcastle disease and Hemorrhagic Enteritis.

The amount of the therapeutic agent utilized in the soft flowable gel is adjusted to provide for the optimum therapeutic dose to the poultry based upon the amount of gel being delivered to the poultry. It has been found that typically each hatchling will ingest between about 0.15 and 0.5 ml of gel within about 5 minutes and the concentration of the therapeutic agent is adjusted to provide the optimum therapeutic dose in this volume of gel. It has been found that typically each larger bird in a barn will ingest between about 0.5 and 1 ml of gel within about 5 minutes and the concentration of the therapeutic agent is adjusted to provide the optimum therapeutic dose in this volume of gel.

The use of the edible polysaccharide gel which gels rapidly is also suitable for adding nitrogen nutrients and other additives such as vitamins to the soft flowable gel. This is especially useful with heat sensitive nutrients which, if exposed to temperatures over about 50° C., are denatured or inactivated.

The amount of the polysaccharide gelling agent is selected to form a soft flowable gel. If too much gelling agent is used the gel is not easily flowable and thus is difficult to pump through the delivery system. If too little gelling agent is used the gel form may not maintain any therapeutic agent contained in the gel such as immunizing organisms in a relatively uniform suspension. In addition, too little gelling agent may also not trap the moisture properly and may allow the water to escape, which can result in reduced viability of the immunizing organisms as well as causing wetting of the birds.

If soft gel beadlets for treating a flock of poultry in any environment are not sufficiently sticky, the gel beadlets can more easily roll off the feathers of the birds onto the floor, particularly in a barn, thereby reducing the availability of the beadlets for the birds' consumption. It has been found that in order to enhance the ability of the gel beadlets to stick to the feathers of the poultry so that they may be ingested as the poultry preen, a mixture of gums or gelling agents is preferably utilized. Thus, in addition to the Carrageenan, one or more additional gums or gelling agents particularly a gum is utilized. Such additional gelling agents include xanthan gum, guar gum, gum arabic, and locust bean gum. Preferably the additional gelling agent is a Xanthan gum and is incorporated in the gel at a final concentration of between 0.05 and 0.15 percent more preferably about 0.1 to 0.15 percent. The addition of xanthan gum, for example, will make the soft gel more "sticky" or increase the adherence of the beadlets to the feathers of the birds. The xanthan gum makes the gel beadlets more sticky or adhere better to the birds' feathers, and increasing the time the gel beadlets can stick to the feathers increases the availability of the beadlets and gives the birds more time to preen and eat the gel beadlets off of the feathers. Guar gum also makes the soft gel beadlets stickier, but it does not provide as much stickiness as xanthan gum. Other gums, such as gum arabic and locust bean gum may also increase the stickiness of soft gel beadlets.

Preferably the one or more gelling agents are provided as a dry powder comprising a mixture containing 20-30% w/w maltodextrin, 60-70% carrageenan, 2-5% carboxymethyl cellulose and 2-6% xanthan gum (60/40 gel diluent of Vetech Laboratories Inc. to which xanthan gum was added, which was used in Examples 2 to 4). More preferably, the one or more gelling agents are provided as a dry powder comprising a mixture containing 22-28% maltodextrin, 62-68% carrageenan, 2-6% xanthan gum and 3-5% carboxymethyl cellulose. Preferably, the one or more gelling agents are provided as a dry powder comprising a mixture containing 25% maltodextrin, 67% carrageenan, 4% xanthan gum and 4% carboxymethyl cellulose. Most preferably, the composition is a water diluent reconstituted from a dry powder mixture containing 20-30% w/w carrageenan (lambda carrageenan), 60-70% maltodextrin, 2-5% carboxymethyl cellulose and 2-6% xanthan gum (Water diluent of Vetech Laboratories Inc. to which xanthan gum was added, which was used in Example 5, where the carrageenan is lambda carrageenan). To make the sticky flowable soft gel, for example, one can take about 50 to 100gm of one of the foregoing dry powder mixtures and mix it with about 4 liters of liquid, such as water. In the resulting sticky flowable soft gel, xanthan gum is present preferably in an amount of about 0.05-0.15% w/v or most preferably in an amount of 0.1% w/v.

It is preferred if the soft gel vaccine of the present invention is provided as a kit for immunizing a flock of poultry. The poultry are preferably a flock of poultry in a barn, such as on a barn floor or in cages, but the poultry can also be a flock of poultry in a hatchery or free range farm. Such kit embodiments of the present invention may comprise a mixture of the one or more gelling agents provided as a dry powder in a first vial and a composition of a sufficient number of live immunogenic organisms to immunize the poultry and a pharmaceutically acceptable excipient in a second vial. More preferably, the kit also includes instructions to reconstitute the gelling agents and live immunogenic organisms, mix the reconstituted agents and organisms and administer them to poultry in a barn, hatchery or free range farm. A kit of an embodiment of the invention may include instructions to add water to the dry powder mixture and mix the hydrated dry powder mixture with the therapeutic agent composition and administer it to a flock of poultry.

The gel form vaccine of the present invention may be dispensed onto the poultry in the barn, hatchery or free range farm by any suitable dispensing apparatus that is capable of forming small beadlets. Preferably for ease of operation a portable hand spray apparatus is utilized with a manifold nozzle arrangement that may be easily directed at the poultry to dispense the beadlets onto the poultry.

The following examples are utilized to illustrate preferred embodiments of the present invention but are not to be construed as limiting the scope of the invention to the specific examples.

Example 1

Tests were conducted to determine the proper amount of the gelling agents to be utilized in the gel form. Mixtures of maltodextrin, carrageenan, and carboxymethyl cellulose (60/40 diluent of Vetech Laboratories Inc. and Water diluent of Vetech Laboratories Inc., as described herein) to which Xanthan gum was added, were tested for their ability to produce a suitable gel. The dry components were mixed with water at final ratios of 0.7 to 1.5% w/v and the thus formed gel was dispensed onto a plastic surface to form small beadlets. The plastic surface was then angled to determine the stickiness of the gel droplets. From the test, it was determined that all of these mixtures worked. For example, one suitable formulation was a dry mixture of about 25% maltodextrin, 67% carrageenan, 4% carboxymethyl cellulose with 4% xanthan gum added and this mixture was utilized in the further tests. All percentages are by weight.

The same tests were conducted wherein xanthum gum was replaced with guar gum. The resulting soft gel with the guar gum was more sticky than using the 60/40 diluent or Water diluent alone, but was less sticky than the soft gel made with the xanthan gum.

Example 2

Infectious Bursal Disease (IBD) Gel Spray Vaccination

Twenty five SPF chicks were used in this test to determine whether the gel spray delivery system can be used to deliver vaccines or biologics to commercial chickens and turkeys beyond the hatchery. Blood samples (~0.5 ml) were collected from the jugular vein of 10 randomly selected chicks a day before vaccination or 6 days of age. At 7 days of age the 25 birds were divided into three groups and vaccinated as follows:
Group 1—Water vaccination by gavage (6 birds)
Group 2—Gel diluents by gavage (6 birds)
Group 3—Gel diluents by hand spray (13 birds)
Vaccine Preparation for Groups 1, 2 and 3:

Vaccine stabilizer was prepared by suspending 0.7 gm of skim milk powder in 250 ml of distilled water. Two third of a vial of IBDV (s-706 Strain) of 2,500 doses was added to this 250 ml of stabilizer to make 1 total of 1,000 doses. To this suspension a suspension of *E. acervulina* were added as markers of vaccine take at 300 oocysts per SPF bird. No further ingredients were added to the Water vaccine of Group 1. For the Gel vaccine preparation of Group 3, two 1 ml syringes were used to withdraw 0.75 ml each of this vaccine suspension with constant agitation. Then, about 6.2 gm of the of 60/40 gel diluent of Vetech Laboratories Inc. as described herein, 0.5 gm xanthan gum and 0.2 gm of food color were then added and all mixed into a suspension and transferred to a 500 ml hand sprayer. The Gel vaccine preparation of Group 2 was identical to that of Group 3, except the suspension was not transferred to a hand sprayer, as the Gel was instead administered by gavage.
Vaccination:

Group 1 birds were vaccinated by gavage of the water suspension of IBD vaccine. Then the 13 Group 3 birds were sprayed with the gel suspended at 0.25 ml per bird (about 4 squirts for the 13 birds). Some vaccines suspension was then sprayed into a clean plastic cup and withdrawn into 1 ml syringe to inoculate the 6 Group 2 birds by gavage at 0.25 ml each.
Vaccine Take:
Coccidial Present as Early Indicators:

One bird each from Groups 1 and 2 and 2 birds from Group 3 were examined on Day 5 post inoculation (PI) for the presence of lesions in the duodenum. The rest of the birds were examined for the presence of oocysts in their fecal collection on Day 6 PI.

Presence of IBD by Elisa Test:

All blood samples by Elisa test for the presence or absence of IBD were carried out by the Laboratory Services of the Animal Health Laboratory of the University of Guelph, Guelph, Ontario.
Summary of Results:

TABLE 1

| | | Coccidia | | | | IBD |
|---|---|---|---|---|---|---|
| Group | Treatment (no. of birds) | Lesions 5 days PI | Oocysts 6 days PI | IBD (Elisa) (−1 day) | IBD (Elisa) 14 days PI | (Elisa) 18 days PI |
| All groups | No treatment | N.D. | | 0/10 | | |
| 1 | Water (gavage) | 1/1 | 4/5 | — | 4/5 | 4/5 |
| 2 | Gel spray (gavage) | 1/1 | 5/5 | — | 5/5 | 5/5 |
| 3 | Gel spray (sprayed) | 2/2 | 6/10 | — | 10/10 | 10/10 |

Example 3

Infectious Bursal Disease (IBD) Gel Spray Vaccination

The above example was repeated with 25 birds divided into 5 groups as follows:
Group 1—No treatment
Group 2—Water Gavage
Group 3—Gel by Gavage
Group 4—Gel+Immucox by Gavage
Group 5—Gel Spray The Gels of Groups 3, 4 and 5 contained 0.1% w/v xanthan gum with 60/40 gel diluent of Vetech Laboratories Inc. The Group 2 treatment did not contain xanthan gum or diluent, only water. Group 1 was a control group and was not treated.

Blood samples (~0.5 ml) were collected from the jugular vein at the relevant days post immunization and all blood samples by Elisa test for the presence or absence of IBD were carried out by the Laboratory Services of the Animal Health Laboratory of the University of Guelph, Guelph, Ontario.
Summary of Results:

TABLE 2

| | | IBD (Elisa) days PI | | | |
|---|---|---|---|---|---|
| Group | Treatment | 8 | 14 | 18 | 21 |
| 1 | None | 0/4 | | | |
| 2 | Water (gavage) | — | — | 4/5 | — |
| 3 | Gel Spray (gavage) | — | — | 4/5 | |
| 4 | Gel spray + Immucox (gavage) | — | 4/5 | — | 6/6 |
| 5 | Gel Spray (Sprayed) | — | — | 8/10 | 3/3 |

Example 4

*Salmonella* Gel Spray Immunization

Twenty five SPF chicks were used in this test to determine if commercially available live *salmonella* vaccine can be uniformly delivered by the Gel-spray method and not be affected by Immucox Coccidiosis Vaccine. Birds were immunized with one or both of *Salmonella* Vaccine: Salmune (Fort Dodge) and IMMUCOX II (Vetech Laboratories).

The Gel-Spray Delivery was delivered with 1.3% w/v of 60/40 gel diluent of Vetech Laboratories Inc. and 0.1% w/v of Xanthan gum was added to increase stickiness. Positive control birds were inoculated by gavage, with the recommended dose of Salmune (0.25 mL) through a 1 mL syringe. Cloacal swabs of negative controls were collected four days before any of the 12 day old SPF birds were inoculated. Gel-spray with vaccine only were plated for colony identification purposes. Gel-sprayed birds were sprayed at a rate of one spray per three birds (or roughly 1RD/bird) with a hand sprayer. (RD=recommended dose)

Results:

TABLE 3

Presence of Salmune colonies after vaccination of birds with gavage and Gel-Spray Method of Delivery.

| Treatment | Route | Cloacal Swab 48 hrs PI | # plates with salmune present/ # of total plates (on SS Agar) 96 hrs @ 37° C. | Characteristics |
|---|---|---|---|---|
| Negative Control | None | Yes | 0/10 | Mixed colonies without Salmune colonies |
| Salmune Only | None | direct plating | 2/2 | Pink, discrete colonies |
| Positive Control | Gavage | Yes 48 hrs PI | 10/10 | 7 plates of pure colonies 3 plates mixed colonies with Salmune present |
| Gel-Spray | Sprayed | Yes 48 hrs PI | 14/15 | 12 plates of pure colonies 3 plates of mixed colonies with Salmune present |

These results show that live *Salmonella* vaccine could be successfully delivered by the Gel-Spray system to chicks in the barn.

Example 5

Newcastle Disease Gel Spray Immunization

Experimental chickens. Broiler chicks were hatched in our laboratory from SPF eggs obtained from Sunrise Farm Inc. and was used throughout the experiments. These chicks were placed in single-use cardboard boxes and housed in a disinfected isolated quarter. Feed and water were supplied ad libitum. At day 9, 25 chicks were divided into three groups. Two groups of 10 chickens were either vaccinated by water or by gel droplets method. Five chicks served as unvaccinated controls.

The gel diluent. The Gel-sprayed vaccines (gel droplet method) were delivered with 1.3% of the Water diluent of Vetech Laboratories Inc. to which 0.1% of Xanthan gum was added. Red food color was added to the mixture as an indicator for vaccine take.

NDV Vaccination: Vaccine stabilizer was prepared by suspending 3 g/liter of skim milk powder in distilled water (Bermudez and Stewart-Brown, 2003). The lyophilized 1000 doses NDV vaccine (B1 type, Fort Dodge) was first dissolved in 4 ml of the vaccine stabilizer, and 3 ml (750 doses) were added to 375 ml of the gel diluent (0.5 ml/chicken). The remaining of the reconstituted vaccine (250 doses) was added to 2.5 liters of the stabilizer, and 10 ml/chicken was used for the water vaccination and given in a gallon-jar drinker.

For Gel Curtain Droplets Vaccination (Gel-sprayed vaccines/gel droplet method), chickens were placed in a cardboard disposable box and sprayed from the top, and left to preen the sprayed vaccine. The reconstituted ND vaccine in the gel was delivered using a hand held sprayer, attached to it a special multi-opening device (header).

Water was withdrawn from chickens of the two groups, for about 2 hours before vaccination.

Blood Sampling:

Blood samples were withdrawn from jugular vein using 1 ml syringes and sera were separated by centrifugation after incubation for 30-60 minutes at 37° C. Samples were collected at 3, 14 and 21 days post vaccination.

Sera were sent to the Animal Health Laboratory, University of Guelph, to test for the presence of antibody response to Newcastle Disease virus using the ELISA method.

TABLE 4

Detection of antibodies to Newcastle Disease vaccine (B1) delivered by gel droplets method in chicken sera by ELISA.

| Groups | 3 days PV* | 2 weeks PV | 3 weeks PV |
|---|---|---|---|
| Water drinker*** | 0/3 ** | 6/10 | 8/9 |
| Gel droplets | 0/3 | 8/10 | 9/10 |
| Controls | 0/3 | 1/5 | 1/5 |

*post vaccination
** Number positive/Number tested.
***gallon-jar drinker

TABLE 5

Mean ELISA titres of the three vaccinated groups at different time post vaccination.

| Groups | 3 days PV* | 2 weeks PV | 3 weeks PV |
|---|---|---|---|
| Water drinker*** | 1 | 2141(3275**) | 2946(3487) |
| Gel droplets | 1 | 788(642) | 2305(2346) |
| Controls | 26 | 122(242) | 159(311) |

*Post vaccination
**Standard deviation.
***gallon-jar drinker

These results show that live New Castle Disease vaccine could be successfully delivered by the Gel-Spray system to chicks in the barn.

The soft flowable gel of the present invention allows for an easy to use system for treating poultry in the barn, hatchery or free range farm. The gel spray allows for rapid and easy administration of bacterial or viral vaccine to poultry in a barn with less effort by the barn workers as compared to prior art methods. In addition, as the method of the present invention requires significantly less handling of the watering systems, the time to immunize the poultry flocks are significantly reduced to a couple of hours as compared to a day or more with the prior art methods.

In a preferred embodiment, the soft gel is used for administering therapeutic agents particularly viral vaccines to poultry in the barn. Examples of therapeutic agents which may be delivered using the soft gel include live vaccines that are that used to immunize poultry including viral vaccines such as Hemorrhagic Enteritis Virus (HE), Infectious Bursal Disease Virus (IBD) and Newcastle Disease Virus (ND). Such vaccines are, at present, comprised of an attenuated strain of the virus in a suitable carrier for administration. Other vaccines for delivery in a soft gel include *Salmonella*, Infectious Bronchitis, Infectious Laryngotracheitis, *mycoplasma* sp., Pneumoviruses and coccidiosis. The soft gel can also be used to deliver therapeutic agents such as probiotics, *lactobacillus* or *bacillus* species, competitive exclusion products such as Broilact, vitamins, electrolytes or water. Any organisms added to the soft gel must be live organisms. All feed has to be pasteurized, which is called pelleting, and that kills harmful organisms, and it also kills helpful organisms including probiotics. One can deliver the vegetative form of probiotics in the soft gel to poultry in the barn, since the soft gel does not go through pelleting, as an alternative. One can also use the sticky soft gel to wet the floor for cocci sporulation purposes, where the therapeutic agent is water.

The use of the soft flowable gel vaccine also allows for the preparation of multivalent vaccines containing more than one organism commonly utilized for vaccination against respiratory diseases such as Newcastle disease virus and bronchitis, *Salmonella* and coccidiosis, and other poultry diseases, as well as probiotics. This flowable gel will keep the multivalent vaccines multivalent by providing uniform suspension of the viral (or bacterial or protozoan) agents until the beadlets are ingested.

The method and soft gel vaccine of the present invention provides for an easy to use means of immunizing a large number of poultry by spraying the vaccine on the poultry in the barn.

All patent and non-patent references referred to in this application are hereby incorporated by reference in their entirety.

Although various preferred embodiments of the present invention have been described herein in detail, it will be appreciated by those skilled in the art that variations may be made thereto without departing from the spirit of the invention or the scope of the appended claims.

I claim:

1. A dry powder mixture comprising:
   a) 2-5% w/w carboxymethyl cellulose;
   b) 2-6% w/w xanthan gum;
   c) 20-30% w/w maltodextrin or carrageenan; and
   d) 60-70% w/w maltodextrin or carrageenan;
   wherein when maltodextrin is present in an amount of 20-30% w/w, then carrageenan is present in an amount of 60-70% w/w, and when carrageenan is present in an amount of 20-30% w/w, then maltodextrin is present in an amount of 60-70% w/w; and
   wherein the dry powder mixture forms a sticky soft flowable gel in suspension in water.

2. The dry powder mixture of claim 1 wherein the sticky gum is xanthan gum provided in an amount to constitute about 0.05-0.15% w/v of the soft flowable gel.

3. The dry powder mixture of claim 1 wherein the carrageenan and the maltodextrin in combination are provided in an amount to constitute about 0.5-2.5% w/v of the sticky soft flowable gel.

4. The dry powder mixture of claim 1 wherein one of the carrageenan and the maltodextrin is provided in an amount to constitute about 1.5-1.75% w/v of the sticky soft flowable gel, and the other of the carrageenan and the maltodextrin is provided in an amount to constitute about 0.5-0.75% w/v of the sticky soft flowable gel.

5. A sticky soft flowable gel composition for use in treating a flock of poultry comprising:
   i) a dry powder mixture comprising:
      a) 2-5% w/w carboxymethyl cellulose;
      b) 2-6% w/w xanthan gum;
      c) 20-30% w/w maltodextrin or carrageenan; and
      d) 60-70% w/w maltodextrin or carrageenan, wherein when maltodextrin is present in an amount of 20-30% w/w, then carrageenan is present in an amount of 60-70% w/w, and when carrageenan is present in an amount of 20-30% w/w, then maltodextrin is present in an amount of 60-70% w/w;
   ii) water; and
   iii) a therapeutic agent.

6. The sticky soft flowable gel composition of claim 5 wherein the carrageenan and the maltodextrin in combination are in an amount of about 0.5-2.5% w/v of the sticky soft flowable gel.

7. The sticky soft flowable gel composition of claim 5 wherein one of the carrageenan and the maltodextrin is in an amount of about 1.5-1.75% w/v of the sticky soft flowable gel, and the other of the carrageenan and the maltodextrin is in an amount of about 0.5-0.75% w/v of the sticky soft flowable gel.

8. The sticky soft flowable gel composition of claim 5 wherein the therapeutic agent is a therapeutically effective amount of at least one therapeutic agent selected from the group consisting of
   a) a live organism selected from the group consisting of Hemorrhagic Enteritis Virus (HE), Infectious Bursal Disease Virus (IBD), Newcastle Disease Virus (ND), *Salmonella*, Infectious Bronchitis, Infectious Laryngotracheitis, *Mycoplasma* sp., a Pneumovirus, Coccidiosis, and a competitive exclusion product, wherein said competitive exclusion product is a probiotic,
   b) vitamins,
   c) minerals, and
   d) electrolytes.

9. A kit for treating a flock of poultry comprising a dry powder mixture in a first container, wherein the dry powder mixture is suspended in water thereby forming a sticky soft flowable gel, and a therapeutic agent in the first container or in a second container, wherein the therapeutic agent is for dissolution or suspension in the sticky soft flowable gel, the dry powder mixture comprising:
   a) 2-5% w/w carboxymethyl cellulose;
   b) 2-6% w/w xanthan gum;
   c) 20-30% w/w maltodextrin or carrageenan; and
   d) 60-70% w/w maltodextrin or carrageenan;
   wherein when maltodextrin is present in an amount of 20-30% w/w, then carrageenan is present in an amount of 60-70% w/w, and when carrageenan is present in an amount of 20-30% w/w, then maltodextrin is present in an amount of 60-70% w/w.

10. The kit of claim 9 wherein the sticky gum is xanthan gum provided in an amount to constitute about 0.05-0.15% w/v of the soft flowable gel.

11. The kit of claim 9 wherein the carrageenan and the maltodextrin in combination are provided in an amount to constitute about 0.5-2.5% w/v of the sticky soft flowable gel.

12. The kit of claim 9 wherein one of the carrageenan and the maltodextrin is provided in an amount to constitute about 1.5-1.75% w/v of the sticky soft flowable gel, and the other of the carrageenan and the maltodextrin is provided in an amount to constitute about 0.5-0.75% w/v of the sticky soft flowable gel.

13. The kit of claim 9 wherein the therapeutic agent is at least one therapeutic agent selected from
   A) in the second container, the therapeutic agent which is
      i) a therapeutically effective amount of at least one live organism selected from the group consisting of Hemorrhagic Enteritis Virus (HE), Infectious Bursal Disease Virus (IBD), Newcastle Disease Virus (ND), *Sal-*

*monella*, Infectious Bronchitis, Infectious Laryngotracheitis, *Mycoplasma* sp., a Pneumovirus, Coccidiosis, and a competitive exclusion product, wherein said competitive exclusion product is a probiotic; and B) in the first container or in the second container, the therapeutic agent which is a therapeutically effective amount of at least one therapeutic agent selected from the group consisting of i) vitamins, ii) minerals, and iii) electrolytes.

14. The kit of claim 13 wherein the therapeutic agent is Infectious Bursal Disease Virus.

15. The sticky soft flowable gel composition of claim 8, wherein the probiotic is a lactobacillus or bacillus species.

16. The kit of claim 13, wherein the probiotic is a lactobacillus or bacillus species.

* * * * *